United States Patent [19]

Reinhardt et al.

[11] Patent Number: 5,425,366
[45] Date of Patent: Jun. 20, 1995

[54] ULTRASONIC CONTRAST AGENTS FOR COLOR DOPPLER IMAGING

[75] Inventors: Michael Reinhardt; Thomas Fritzsch; Dieter Heldmann; Joachim Siegert, all of Berlin, Germany

[73] Assignee: Schering Aktiengesellschaft, Berlin and Bergkamen, Germany

[21] Appl. No.: 72,748

[22] Filed: Jun. 7, 1993

Related U.S. Application Data

[63] Continuation-in-part of Ser. No. 536,377, Jun. 11, 1990, which is a continuation-in-part of Ser. No. 305,820, Feb. 3, 1989, abandoned.

[30] Foreign Application Priority Data

Feb. 5, 1988 [DE] Germany .................. 38 03 972.9
Jun. 13, 1992 [DE] Germany .................. 42 19 724.4

[51] Int. Cl.$^6$ ............................................. A61B 8/00
[52] U.S. Cl. ............................................. 128/662.02
[58] Field of Search ............... 128/660.02, 662.02; 424/9, 11

[56] References Cited

U.S. PATENT DOCUMENTS

| | | | |
|---|---|---|---|
| 4,276,885 | 7/1981 | Tickner et al. | 128/662.02 |
| 4,689,986 | 9/1987 | Corson et al. | 128/660.02 X |
| 4,774,958 | 10/1988 | Feinstein | 128/662.02 |
| 5,215,093 | 6/1993 | Miyazaki et al. | 128/661.09 |

FOREIGN PATENT DOCUMENTS

| | | |
|---|---|---|
| 1232837 | 2/1988 | Canada . |
| 1239092 | 7/1988 | Canada . |
| 0052575 | 5/1982 | European Pat. Off. . |
| 0077752 | 4/1983 | European Pat. Off. . |
| 0122624 | 10/1984 | European Pat. Off. . |
| 0123235 | 10/1984 | European Pat. Off. . |
| 0224934 | 6/1987 | European Pat. Off. . |
| 0327490 | 8/1989 | European Pat. Off. . |
| 0441468 | 8/1991 | European Pat. Off. . |
| 0484181 | 5/1992 | European Pat. Off. . |
| 38 03 972.9 | 2/1988 | Germany . |
| 3803972 | 8/1989 | Germany . |
| WO89/06978 | 8/1989 | WIPO . |
| WO91/15999 | 10/1991 | WIPO . |
| WO93/00991 | 1/1993 | WIPO . |

OTHER PUBLICATIONS

Becher et al., "Improved Sensitivity of Color Doppler by SH U 454", *The American Journal of Cardiology*, vol. 64, No. 5 (Aug. 1, 1989), pp. 374–377.

R. Omoto et al., "The Development of Real-Time Two-Dimensional Doppler Echocardiography and Its Clinical Significance in Acquired Valvular Diseases With Special Reference to the Evaluation of Valvular Regurgitation", *Jpn. Heart J.*, vol. 25, No. 3, pp. 325–340 (May 1984).

W. J. Bommer et al., "Real ∝ Time Two-Dimensional Color-Flow Doppler: Enhanced Doppler Flow Imaging in the Diagnosis of Cardiovascular Disease", *Am. J. Cardiol.*, vol. 49, p. 944 (Mar. 1982), abstr.

K. Miyatake et al., "Clinical Applications of a New Type of Real-Time Two-Dimensional Doppler Flow Imaging System", *Am. J. Cardiol.*, vol. 54, pp. 857–868 (Oct. 1, 1984).

J. Roelandt, "Contrast Echocardiography", *Ultrasound in Med. & Biol.*, vol. 8, No. 5, pp. 471–492 (1982).

Gramiak, "Echocardiography of the Aortic Root", *Invest. Radiol.*, vol. 3 (Sep.–Oct. 1968), pp. 356–366.

Ophir et al., "Ultrasonic Backscatter From Contrast Producing Collagen Microspheres", *Ultrasonic Imaging*, vol. 2, pp. 66–67 (1980).

Ophir et al., "Aqueous Solutions as Potential Ultrasonic Contrast Agents", *Ultrasonic Imaging*, vol. 1, pp. 265–279 (1979).

Tyler et al., "In-vivo Enhancement of Ultrasonic Image Luminance by Aqueous Solutions with High Speed of Sound", *Ultrasonic Imaging*, vol. 3, pp. 323–329 (1981).

Mattrey et al., "Ultrasonic Enhancement of Myocardial Infarction with Perfluorocarbon Compounds in Dogs", *Am. J. Cardiol.*, vol. 54, pp. 206–210 (Jul. 1, 1984).

*Primary Examiner*—Francis Jaworski
*Attorney, Agent, or Firm*—Millen, White, Zelano, & Branigan

[57] ABSTRACT

The invention relates to a method for obtaining an ultrasonic image of a patient with ultrasonic color Doppler modality with microparticulate ultrasonic contrast agents in regions where the ultrasonic contrast agents are essentially motionless.

19 Claims, 6 Drawing Sheets

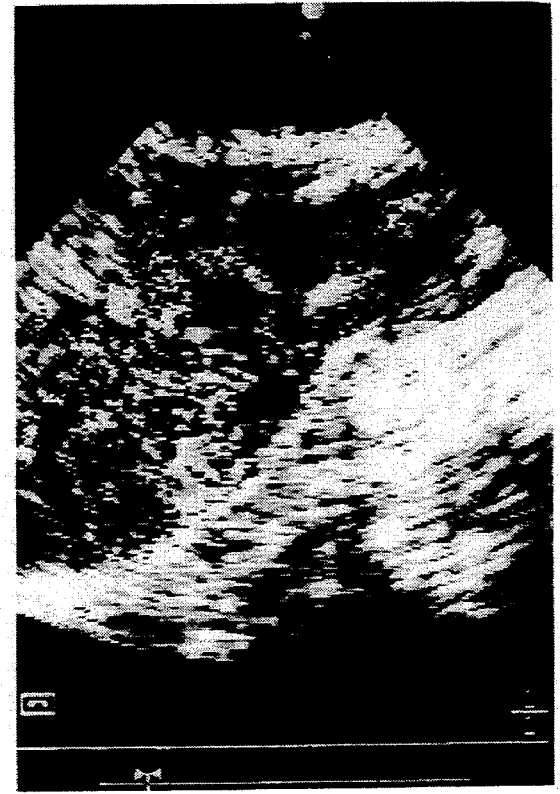
FIG. IA              FIG. IB

FIG. 4A
FIG. 4B
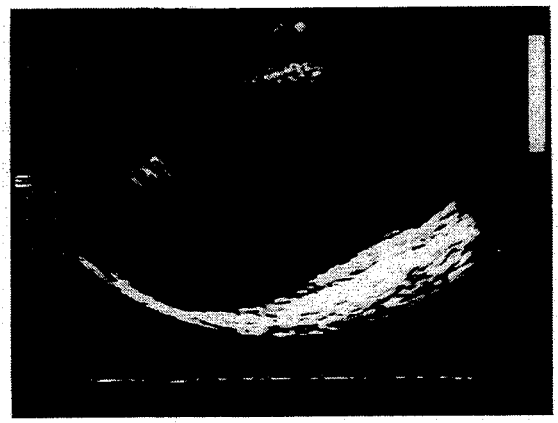
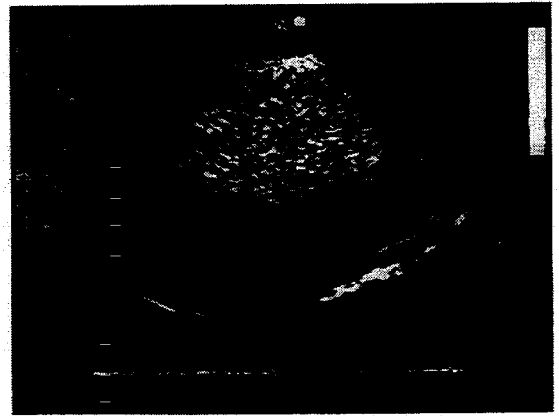
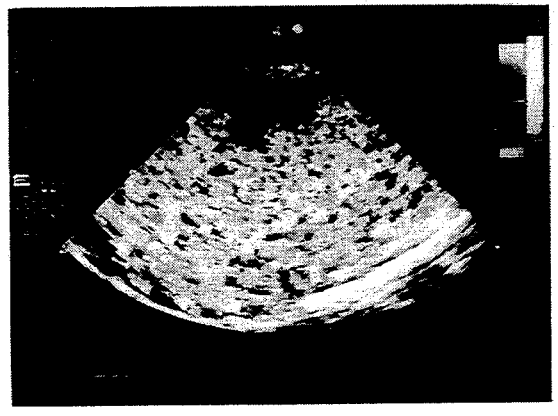
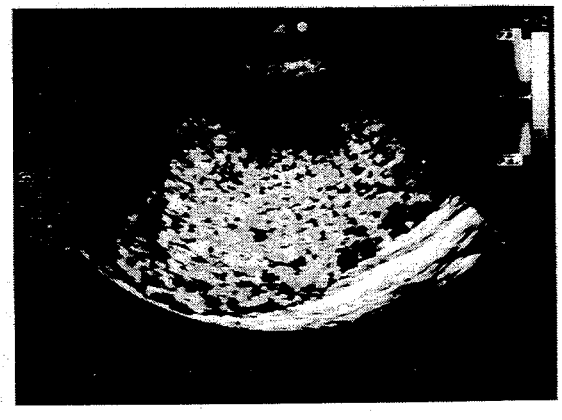
FIG. 4C
FIG. 4D

ULTRASONIC CONTRAST AGENTS FOR COLOR DOPPLER IMAGING

CROSS-REFERENCE TO RELATED APPLICATIONS

This application is a continuation-in-part application of Ser. No. 07/536,377, filed Jun. 11, 1990, which is a continuation application of Ser. No. 305,820, filed Feb. 3, 1989, and now abandoned each of which is entirely incorporated by reference herein.

BACKGROUND OF THE INVENTION

The invention relates to use of microparticles which are microcapsules containing a gas or volatile organic fluid, to obtain images in a Doppler-type ultrasonic mode (sonography) in diagnostic processes, as well as to processes for preparation of such microcapsules.

Various ultrasonic imaging techniques, scanners and imaging modes are known, some of which have different objectives. For example, the echo cardiographic techniques described by Hilman (CA 1,232,837) are said to provide a 2-D echo image or an M-mode echo image of how blood marked by a contrast agent travels through the heart. Tickner et al. (U.S. Pat. No. 4,276,885) indicate that detecting the Doppler shift frequency from the backscatter of bubbles provides a velocity profile for measurement of cardiac output. Doppler modes for ultrasonic imaging include CW Doppler, PW Doppler and color Doppler techniques. Doppler techniques based on signals from ultrasound reflective bodies heretofore have required flowing bodies whose motion forms the basis for the Doppler effect. These quantify the rate and flow direction of moving structures, generally blood flows, by the Doppler shift caused by the red blood cells flowing through the ultrasonic field. See:

1. Omoto, R., Yokote, Y. Takamoto, S., et al: The development of real time two dimensional Doppler echo-cardiography and its clinical significance in acquired valvular disease with special reference to the evaluation of valvular regurgitation. Jpn Heart J 25:325-340, 1984;
2. Bommer, W. J., Miller, L.: Real time two dimensional color flow Doppler: Enhanced Doppler flow imaging in the diagnosis of cardiovascular disease. Am. J. Cardiol. 49:944, 1982 (abstr.);
3. Miyatake, K., Okamoto, M., Kinoshita, N., et al: clinical application of a new type of real-time two dimensional Doppler flow imaging system, Am. J. Cardiol. 54:857-868, 1984; and
4. Omoto, R. (1987) Real time two-dimensional Doppler echocardiography. 2nd Ed., Lea & Febiger, Philadelphia; for details of prior art color Doppler procedures where different Doppler frequencies are displayed as different colors.

On the other hand, it is known that cardial echo contrasts can be achieved through peripheral injection of solutions which contain fine gas bubbles (Roelandt, J., Ultrasound Med. Biol. 8:471-492, 1982). See also Gramiak, Invest. Radiol 3 (1968) 356/366. These gas bubbles are obtained in physiologically compatible solutions, e.g., through shaking, other agitation or through the addition of carbon dioxide. See EP 77,752 and Roelandt, supra. In addition, there are ultrasonic contrast agents in the form of particles (Ophir, Gobuty, McWhirt, Maklad, Ultrasonic Backscatter from Contrast-producing Collagen Microspheres, Ultrasonic Imaging 2:66-67 (1980)). Furthermore, solutions of a higher density are used as ultrasonic contrast agents (Ophir, McWhirt, Maklad, Aqueous Solutions as Potential Ultrasonic Contrast Agents, Ultrasonic Imaging 1:265-279 (1979), as well as Tyler, Ophir, Maklad, In-vivo Enhancement of Ultrasonic Image Luminance by Aqueous Solutions with High Speed of Sound, Ultrasonic Imaging 3:323-329 (1981)). It is also known to use emulsions as ultrasonic contrast agents (Mattrey, Andre, Ultrasonic Enhancement of Myocardial Infarction with Perfluorocarbon Compounds in Dogs, Am. J. Cardiol. 54:206-210 (1984)). Other known contrast agents include the gas bubbles of EP A 2 123 235 and 0 122 624, which correspond to CA 1,232,837 and CA 1,239,092, the gas-filled gelatine or albumin hollow bodies of U.S. Pat. No. 4,774,958 (Feinstein), which corresponds to EP A2 0 224 934, and the microbubbles (gas encapsulated in gelatins of U.S. Pat. No. 4,276,885 (Tickner et al.). All these agents are generally useful in one or more of the known ultrasound imaging modalities, e.g., M-mode, B-mode, various Doppler forms known or published, etc.

In EP 0 052 575, gas bubbles are produced by a solid crystalline substance, such as, for example, galactose, being suspended in a carrier liquid. The gas bubbles originate in this case from gas enclosed in cavities or from gas adsorbed on the crystal surfaces. EP 0 122 624 describes a similar contrast medium based on a non-surface-active substance, such as, e.g., galactose, to which a surface-active substance, such as, e.g., magnesium stearate is admixed, which results in a stabilization of the gas bubbles. Thus, the contrasting of the left side of the heart, as well as of various organs, such as liver, spleen and kidney, was also possible in the 2D-echo image or in the M-mode echo image. DE 38 63 972 discloses gas-filled or liquid-filled microcapsules based on biodegradable polymers, such as, e.g., polycyanoacrylates or $\alpha$-, $\beta$-, $\gamma$-hydroxycarboxylic acids. Similar microcapsules are described in European patent application EP 0 441 468. In contrast to the particles disclosed in DE 38 03 972, the particle shell in this case consists of polyaldehydes. EP 0 224 934 and U.S. Pat. No. 4,276,885 describe gas-filled microcapsules based on proteins or albumins (EP) or based on gelatin (US). The particles of DE 38 03 972 and EP 0 441 468 have in common that they are sufficiently stable and sufficiently small ($<10$ $\mu$m) to pass through capillaries and to be taken up intracellularly in the reticulo-endothelial system (such as, e.g., liver, lymphatic nodes and spleen). But the contrasting in using the B-mode or M-mode technique is not in all cases satisfactory, e.g., differentiating healthy tissue (e.g., liver, spleen, lymphatic nodes) from tumor tissue, which contains only few cells belonging to the reticulo-endothelial system, is often not possible. In addition, the representation of the gastrointestinal tract as well as the perfusion of the myocardium causes difficulties.

Thus, the methods for utilizing these contrast agents have not always provided sufficient signal intensity to represent organs, particularly non-cardiac organs. Quantification of selective concentrations of these contrast agents within organs has not been possible. Particularly in the Doppler techniques, it has been necessary heretofore to utilize contrast giving agents (e.g., the mentioned ultrasound contrast agents) in motion (e.g., perfusion) as a source of the Doppler-based imaging.

BRIEF DESCRIPTION OF THE DRAWINGS

Various objects, features and attendant advantages of the present invention will be more fully appreciated as the same becomes better understood when considered in conjunction with the accompanying drawings, in which like reference characters designate the same or similar parts throughout the several views, and wherein:

FIGS. 1A and 1B show Dopper images of a tumorous liver in color Doppler (FIG. 1B) and B mode (FIG. 1A) (Example 24);

FIGS. 4A and 4D show a color Doppler image of a beagle dog bladder (Example 30);

SUMMARY OF THE INVENTION

Figure 2:
FIGS. 2 and 3 show a color Doppler image of a beagle dog stomach lumen and small intestine, respectively (Example 29)

Surprisingly, it has now been found that certain types of microparticles administered to a patient provide effective signal contrast and signal intensity of portions of the patient in which the microparticles are situated when imaged with ultrasonic radiation in the color Doppler mode despite the essential lack of motion of these microparticles in these patient sites, e.g., organs and other tissue. For example, when the microcapsules of U.S. Ser. No. 536,377 were used to image the liver using the conventional B-mode process, no good images and no good contrast were obtained. Surprisingly and contrary to conventional theory, although these particles are essentially motionless when situated in the liver, a color Doppler-based image of the liver containing such particles provides good images and contrast.

Thus, this invention relates to a method of obtaining an ultrasonic image of a patient comprising administering to the patient microparticles comprising cavities filled with a gas or a volatile fluid, which particles upon exposure to color Doppler modality produce a Doppler signal when the particles are essentially motionless in the patient, and imaging said patient with ultrasonic color Doppler modality in a region where said microparticles are essentially motionless.

By "essentially motionless" is meant that the particles are indeed fully motionless or at most are moving at a velocity significantly lower than that of the bloodstream (i.e, those normally imaged by Doppler techniques), e.g., at a velocity on the order of microparticles adsorbed, e.g., into the reticuloendothelial system (RES) and situated in the liver or spleen or situated in other organs, body cavities, the myocardial system, the GI tract or the lymphatic system (e.g., lymph nodes). Thus, microparticles providing an image by this invention are typically moving orders of magnitude more slowly than are microparticles entrained in the venous blood and those imageable by the conventional Doppler technique.

Although not wishing to be bound to theory, it is felt that the images producible by this invention are due to an ultrasound-induced bursting of the capsule walls, which event generates Doppler-sensitive signals (acoustically stimulated acoustic emission).

For example, in the B-mode, the bubbles do not burst. As a result, the irradiated ultrasonic signal has only a small penetration depth into the tissue (because most of the beam is reflected from the contrast media after a few millimeters). This results in a photograph which is homogeneously shadowed. So it is impossible to see tumors in lower tissue layers. In contrast, since in the color Doppler mode the bubbles are believed to burst (because the irradiated energy is higher), they can no longer reflect the irradiated signal. Accordingly, the ultrasonic signal also reaches deeper tissue layers.

Further, it is surprising that the contrast achieved by the invention is better than that achievable with the conventional methods (B-mode, M-mode). This results in a clear improvement of the diagnostic informative value.

Thus, e.g., in the examination of liver tissue by color Doppler sonography, after intravenous injection of the contrast medium, tumor areas (which, as is generally known, contain no or only a few cells capable of absorbing the particles) are imaged in the customary gray-scale values; however, healthy tissue is surprisingly colored (see FIG. 1/right half of the image). A comparison photo in B-mode, which was taken under otherwise identical conditions (see FIG. 1/left half of the image) confirms the clearly improved diagnostic informative value of the color Doppler shot. Tumor areas can no longer be differentiated from the healthy areas.

Analogous color Doppler images of the GI-tract and the lymphatic system, for example, are also obtainable.

For example after oral administration, labeling of the gastric canal is possible, which, e.g., makes possible a differentiation of intestinal structures from other abdominal organs. A representation of the joint cavity is also possible after administration of the contrast medium. Using the Doppler technique of this invention, imaging of the tubes and the cavity of the uterus are also imageable.

Microparticles useful in this invention generally comprise a layer of a material, e.g., a synthetic polymeric-type substance, defining a closed, hollow space, (spherical, spheroidal, ellipsoidal or otherwise), e.g., are microcapsules of such shapes. The coating thickness is preferably as thin as possible, e.g., 10–200 nm, typically about 100 nm or less. The size of the microcapsules will vary with the cavity, organ, tissue or other region being imaged and mode of administration. Thus, of course, for intravenous administration the size will be relatively small, e.g., less than 10 $\mu$m or less than 5 $\mu$m, e.g., 1–2 $\mu$m. For oral administration or in examinations of body cavities, size is not such a critical factor from a safety point of view and larger particles are possible—suitable particle sizes are in the range of, e.g., 1–100 $\mu$m, preferably 10–100 $\mu$m.

The cavities of the microparticles are filled with gases or volatile substances, e.g., having a boiling point below 60° C., preferably gaseous at physiological temperatures.

Suitable microparticles include those described in copending parent application Ser. No. 07/536,377, filed Jun. 11, 1990, and other microparticles comprising polymeric material entrapping gases and/or volatile fluids, e.g., having a boiling point below 60° C. in free or bonded form, e.g., encompassing, entraining, absorbing, etc., the same. Other examples include the "microbubbles" of Tickner et al., U.S. Pat. No. 4,276,885 (gelatin-encased) and Feinstein, U.S. Pat. No. 4,774,958 (protein-, e.g., albumin-encased), e.g., partially denatured albumin or HSA. Any conventional method of denaturing can be used, such as disclosed in the cited references. Also suitable are the polyaldehyde encased microbubble-type particles of U.S. Ser. No. 07/653,792, filed Feb. 11, 1991, and now abandoned i.e., gas- or liquid-filled microcapsules based on biodegradable polymers, which consist of polymerizable aldehydes, which optionally contain additives and/or cross-links capable of copolymerization, optionally surfactants or surfactant mixtures, coupling agents as well as biomolecules or macromolecules optionally bound by these coupling agents. These entire disclosures are incorporated by reference herein.

The contrast agents useful herein which are based on the microparticles disclosed in copending application Ser. No. 07/536,377, filed Jun. 11, 1990, have a determinable and reproducible volume, a considerably longer service life than contrast agents previously known, offer good compatibility without allergic potential and can be concentrated intracellularly in the liver, spleen and/or the lymphatic system via RES uptake. These particles are also suitable as contrast media for color Doppler imaging of the gastrointestinal tract, the myocardial system and body cavities. The microbubbles based on gelatin and albumins useful herein can also be concentrated intra-cellularly in RES and the other locations as can the others mentioned above, e.g., in view of their sizes.

Preferred contrast agents used in the present invention include microparticles of Ser. No. 07/536,377 which consist of a synthetic biodegradable polymer and a gas and/or a fluid with a boiling point below 60° C. Polyesters of $\alpha$-, $\beta$-, $\gamma$- or $\epsilon$-hydroxy carbonic acids, polyalkylcyanoacrylates, polyamino acids, polyamides, polyacrylated saccharides or polyorthoesters are suitable synthetic biodegradable polymers for use in the particle coatings.

The following have proved particularly suitable: polylactic acid, poly-$\epsilon$-caprolactone, copolymers of lactic acid and glycol acid or $\epsilon$-caprolactone, polyhydroxybutyric acid, polyhydroxyvaleric acid, copolymers of hydroxybutyric and hydroxyvaleric acid, polymers of glutamic acid and/or lysine, polydioxanone, polymers or copolymers of amino acids and/or terephthalic aid, phthalic acid or sebacic acid, polyacryldextran, polyacryl starch, polyacrylamide, polyurethane, polyester, polyacetal, polyaminotriazol or polyalkylcyanoacrylate.

Particularly preferred are polybutylcyanoacrylatebased microparticles.

The microparticles contain gases and/or fluids with a boiling point below 60° in free or bonded form. The use of a gas-fluid mixture in the ultrasonic contrast agents is likewise possible. Gases used can be, for example, air, nitrogen, inert gases, hydrogen, carbon dioxide, ammonia, oxygen, methane, ethane, propane, butane, ethylene or other hydrocarbons or their mixtures. Preferred fluids which can be included are: 1,1-dichloroethylene, 2-methyl-2-butene, isopropyl chloride, 2-methyl-1,3-butadiene, 2-butyne, 2-methyl-1-butene, dibromodifluoromethane, furan, 3-methyl-1-butene, isopentane, diethylether, 3,3-dimethyl-1-butyne, dimethylaminoacetone, propylene oxide, N-ethylmethylamine, bromomethane, N-ethyldimethylamine, methylene chloride, pentane, cyclopentane, 2,3-pentadiene, cyclopentene or mixtures thereof.

The microparticles can also contain substances with low steam pressures and/or low boiling points. The physiological isotony can be set by the addition of osmotically active substances such as sodium chloride, galactose, glucose or fructose.

An advantageous process for preparing such ultrasonic contrast agents according to the invention comprises dissolving a polymer or copolymer in one or more organic solvents which are not miscible with water, followed by dispersion in water, possibly with the addition of a further solvent, and then filtering and, if required, drying the emulsion obtained. A further process comprises dissolving a polymer or copolymer in one or more solvents which contain gas bubbles, after which it is precipitated or emulsified in water, if required, with the addition of a further solvent or a further polymer, and then the suspension or emulsion which has been obtained is then filtered and, if required, dried. The freeze-drying process is also suitable as a finishing process.

The freeze drying of the microparticles according to the invention advantageously takes place by adding substances which protect the particles in freeze drying from destruction and/or agglomeration (so-called cryoprotectors). As cryoprotectors, biopolymers (e.g., albumin, autoclaved gelatin, oxypolygelatin, gelatinpolysuccinate, crosslinked polypeptides, synthetic macromolecular substances (for example, povidone, polyvinyl alcohol), sugars (e.g., saccharose, lactose, trehalose, raffinose), sugar alcohols (e.g., mannitol, sorbitol) or mixtures of these pharmaceutical auxiliary agents can advantageously be added in a concentration of 1% to 15% to the suspension. The addition of the cryoprotectors according to the invention takes place either in the production medium, by absorption of the microparticles after the separation by flotation in the cryoprotector solution, or by adding to the suspension directly before the freeze drying.

Surprisingly, it has been found that it can be advantageous, in addition to the cryoprotector, to add a substance, optimizing the freeze drying, from the group of polyols (e.g., glycerol, propylene glycol) or DMSO in a concentration of 0.1 to 3%.

The freeze drying advantageously takes place so that a flotation of the microparticles according to the invention during freezing is prevented. For this purpose, it is advantageous to precool the suspension of the microparticles according to the invention, to freeze it with a freezing rate of 2 kelvin per minute or more and to freeze-dry it.

In the process described, the solvents used can be, for example, furan, pentane, acetone, dioxane, ethyl acetate, xylol, methylene chloride, cyclohexane or hexane or solvent mixtures. Emulsifiers can also be added to the emulsion.

In a further variation of the manufacturing process instead of polymers, monomers are used as the starting product from which the polymer is formed. With this process, a monomer is dissolved in one or more organic solvents and then emulsified in 5-30 parts water or 0.01-0.1N hydrochloric acid, if required with the addition of emulsifiers or buffer substances at a temperature below the boiling point of the organic solvent, after which a 0.2%-20% aqueous solution of a second monomer or, if required, the solution of a substance increasing the pH-value is added to this emulsion and dried, if required.

In another method of operation a monomer is dissolved or dispersed in one or more fluids containing gas bubbles, if required with the addition of emulsifiers or buffer substances. If required, a 0.2%–20% solution of a second monomer or a substance increasing the pH-value in dissolved or gaseous form is added to this solution or dispersion and dried, if required.

By way of example, terephthaloyl- or sebacoyl-chloride or cyanoacrylic acid ester is used as a first monomer, L-lysine as the second monomer and, for example, 2-methyl-1,3-butadiene, dioxane, methylene chloride, toluene or cyclohexane is used as the organic solvent.

According to a further process, the ultrasonic contrast agents are prepared by producing gas bubbles in a 0.5–10% aqueous solution or dispersion of a monomer which contains, if required, additives such as emulsifiers (0.01–5%) or quasi emulsifiers (0.1–5%), and then by adding a cross-linking substance and/or a reaction starter.

In a preferred production process for these particles, monomeric cyanoacrylate in an acidic, aqueous solution saturated with a gas or gas mixtures, which optionally contains at least one surface-active substance, is dispersed with a rotor-stator mixer, the particles obtained after 5 minutes to 3 hours of dispersing are separated, are optionally washed with water, then are taken up in a pharmaceutically acceptable suspension medium and freeze-dried, and the suspension is advantageously moved vigorously during the freezing.

Preferably, butyl ester is used as cyanoacrylate and air, nitrogen, oxygen, noble gases or carbon dioxide are used as gas. Instead of the rotor-stator mixer, comparable devices (such as, e.g., a dissolver-stirrer) can also be used, which allow a vigorous dispersing of the mixture. As a surface-active substance, a substance (substances) from the group of polysorbates, octyl or nonyl phenols, macrogol-glycerol esters or cetomacrogols or Poloxamers ® or their mixtures is (are) used. The pH of the aqueous gas-saturated solution is preferably between 1.8 and 4.5. For adjustment of the pH, especially hydrochloric acid and phosphoric acid are suitable. The separation of the particles takes place by centrifugation or flotation. As a suspension medium, water is suitable for injection purposes optionally with an addition of common salt and/or glucose and/or mannitol and/or lactose, which optionally in addition also contains a surface-active substance, such as, e.g., from the group of polysorbates, octyl or nonyl phenols, macrogol-glycerol esters or cetomacrogols or substances from the group of Poloxamers ® or their mixtures and/or a multivalent alcohol.

In a preferred process for the production of particles based on polyesters an $\alpha$-, $\beta$- or $\gamma$-hydroxycarboxylic acid, optionally together with a water-dispersible emulsifier, is dissolved in a solvent harmless to health, and this solution is added under dispersion with a dissolver-stirrer or a sound rod to a gaseous liquid which, provided that the emulsifier was not already added together with the polyester, contains a water-dispersible emulsifier, the particles obtained after 30 minutes to 2 hours of dispersing are separated, are optionally washed with water, then are taken up in a pharmaceutically acceptable suspension medium and freeze-dried.

According to the invention, polymers of lactic acid or glycolic acid as well as their copolymers are preferred. As harmless solvent, heated ethyl alcohol is preferably used. As a gaseous liquid, water or glycerol 87% is preferably used. The preferred gases are air, nitrogen, oxygen, noble gases or carbon dioxide. As water-dispersible emulsifier, phosphatidylcholine or sucrose-palmitate-stearate 15 as well as their mixtures can be mentioned. As a pharmaceutically acceptable suspension medium, the same media as in the case of the particles based on polycyanoacrylate are suitable. For further details of these processes see German Application 4 219 724, of Jun. 13, 1992, whose disclosure is entirely incorporated by reference herein.

Suitable imaging modalities include any which are capable of selectively imaging the essentially motionless microcapsules discussed herein when situated in the body. These will generally include any modality providing a capability of applying sonic pressure pulses (an inherent aspect of the modalities) to the patient area of interest sufficient to burst the microcapsules, e.g., of at least about 0.2 MPa (peak value in situ), preferably 0.3–0.6 MPa or more, but generally not more than about 1.5 MPa at frequencies in the range of about 1–8 MHz, preferably 2–5 MHz.

The preferred time delay between i.v. injection of microcapsules and start of data acquisition (imaging) depends on the area of interest (i.e, the aims of the diagnostic procedure). Typically, examination by color Doppler can be conducted 1–60 minutes after administration to a patient, e.g., mammals including humans, the optimal time being determined routinely according to the target organs. Typical preferred values are:

10 seconds in examinations of the myocardium,
1–60 minutes p.i. in examinations of the RE system,
5–10 minutes p.i. in examinations of the lymphatic system,
5–60 minutes in gastrointestinal examinations.

In the case of body cavities and bladder examinations, the examination can be started immediately after the introduction of the contrast medium. Following oral administration, the microcapsules can be detected during their passage of the gastrointestinal tract.

This invention can be used with special advantage in contrasting the gastrointestinal tract. In the usual ultrasound methods not amplified by contrast media, the representation of the structures of the gastrointestinal tract has often proved difficult. In particular, the anatomical assignment of the intestinal portions is generally difficult. However, it has now been shown that after oral administration of suspensions of the microcapsules of this invention, a labeling of the gastrointestinal tract was possible by using the color Doppler modality. Thus, for example, defining the limits of intestinal structures from other abdominal organs becomes possible, and functional diagnosis by representation of the gastrointestinal tract is also possible.

In further tests, it has now been shown that microcapsules of this invention also result in diagnostically usable color Doppler ultrasonic effects in the bladder and kidney. Further, administration in joint cavities for the representation of the joint cavity, and transcervical administration for the representation of the uterine cavity and of the tubes have also proved diagnostically effective. Since these administrations do not require intravascular injection, the upper limit of the particle diameter is not limited. Particles with a diameter of about 10–100 microns have proved to be especially advantageous.

Unless indicated otherwise herein, the obtaining of the color Doppler images for any of the foregoing purposes is fully conventional as disclosed in the reference cited above.

The application of the agents is typically, for example, by injection. However, peroral, intraarticular, intravesical, transvaginal and intraperitoneal administration are also suitable in conventional dependence on the organ whose image is desired.

Unless indicated otherwise herein, details, e.g., dosages and procedures, etc., are in accordance with those used for analogous agents in ultrasound imaging, e.g., as described in the publications mentioned herein, all of which are fully incorporated by reference. Dosages depend on the target organ and can be routinely determined. For example, for the liver, 1 ml of contrast medium/kg of body weight is suitable, where the contrast medium contains about $10^9$ particles/ml. In the kidney and many other organs, lower dosages can be used, e.g., typically only about 10% of this dose will suffice. Most routinely determinable, functional dosages will provide about $10^5$–$10^7$ particles per cm$^3$ of target organ. If the evaluation is made by visual inspection of a real time image (conventional color Doppler image) the particle concentration is $10^5$–$10^7$ particles/cm$^3$.

To achieve such a particle concentration in the target organ, it is necessary to administer the contrast medium in the concentrations such as, for example:

| | |
|---|---|
| GI tract | $10^8$–$10^{10}$ particles/kg body weight |
| lymphatic system | $10^7$–$10^9$ particles/kg body weight |
| liver, spleen, (RES system) myocardium and others | $10^7$–$10^9$ particles/kg body weight. |

The maximum concentration of a ready mixed contrast media of this invention is typically $2 \times 10^{10}$ particles/ml.

The process of the present invention can be used to detect tumors in the spleen or liver in that the microparticles are absorbed by the normal tissue of the reticuloendothelial system but not the tumor cells since the latter do not form part of the RES. Examination of these organs with color Doppler techniques thus will show the healthy tissue as colored while the particle-free tumor areas give the usual half-tone (gray scale) images.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

The entire disclosures of all applications, patents and publications, cited above and below, and of corresponding applications Federal Republic of Germany P 38 03 972.9, filed Feb. 5, 1988, and German applications P 4 219 724 and P 4 219 723, each filed Jun. 13, 1992, are hereby incorporated by reference.

EXAMPLES

Example 1

500 mg polylactide were dissolved in 4 ml furan and 0.6 ml cyclohexane and this solution was emulsified in 40 ml of a 0.1% solution of polyoxyethylene polyoxypropylene polymer with a molecular weight 12.0000 (Pluronic ® F 127), with the temperature being kept beneath 15° C. during emulsifying. The temperature was then slowly raised to evaporate off the organic solvent. The resulting suspension was then freeze-dried.

Example 2

300 mg α-cyanoacrylic acid butyl ester were dissolved in 1 ml furan and this solution was emulsified in 10 ml 0.1N hydrochloric acid which contained 1% polyoxyethylene polyoxypropylene polymer with a molecular weight 12.000 (Pluronic ® F 127), with the temperature being kept beneath 15° C. during emulsifying. At the end of polymerization, the resulting suspension was freeze-dried.

Example 3

200 mg α-cyanoacrylic acid butyl ester were dissolved in 0.4 ml isoprene and emulsified in 30 ml 0.01N hydrochloric acid which contained 1% polyoxyethylene polyoxypropylene polymer with a molecular weight 8.350 (Pluronic ® F 68), with the temperature being kept beneath 10° C. during emulsifying. At the end of the polymerization, the suspension was neutralized with 0.1N NaOH and isotonized with sodium chloride.

Example 4

400 mg α-cyanoacrylic acid butyl ester were dissolved in 0.4 ml methylene chloride and emulsified in 60 ml 0.01N hydrochloric acid which contained 1% polyoxyethylene polyoxypropylene polymer with a molecular weight 12.000 (Pluronic ® F 127), with the temperature being kept beneath 10° C. during emulsifying. At the end of polymerization, the suspension was neutralized with 0.1N soda lye and isotonized with sodium chloride.

Example 5

400 mg polycaprolactone were dissolved in 6 ml furan and 0.3 ml cyclohexane and emulsified in 60 ml 1% polyoxyethylene polyoxypropylene polymer with molecular weight 12.000 (Pluronic ® F 127), with the temperature being kept beneath 15° C. The temperature was then slowly raised to evaporate off the organic solvent. The resulting suspension was then freeze-dried.

EXAMPLE 6

400 mg terephthalic acid dichloride were dissolved in 2 ml furan and then emulsified in 50 ml 3% sodium carbonate solution which contained 0.1% polyoxyethylene polyoxypropylene polymer with a molecular weight 12.000 (Pluronic ® F 127). After the addition of 60 mg L-lysine, dissolved in 5 ml 0.1% Pluronic ® F 127, the micro capsules were centrifuged and washed several times with 0.1% Pluronic ® 127 solution. Before use the suspension was isotonized with sodium chloride.

Example 7

0.4 ml of cyanoacrylic acid butyl ester is dispersed in 60 ml of HCl of pH 2.0, which contains 1% Poloxamer 407, with a rotor-stator mixer for 5 minutes. The microparticles with an average size of 2 μm are centrifuged off and taken up in 300 ml of an aqueous solution of 1% Poloxamer and 5% glucose. The density determination produces a specific weight of 0.2 g/cm$^3$.

Example 8

The procedure is as in Example 7, and the hydrochloric acid exhibits a pH of 2.5 and Poloxamer 407 is replaced by octoxynol-9. The microparticles have an average size of about 0.9 μm and a specific weight of 0.2 g/cm³ They are taken up in 300 ml of a 5% mannitol solution, which contains 0.1% polysorbate 20.

Example 9

The procedure is as in Example 7, and the hydrochloric acid has a pH of 3.0 and Poloxamer 407 is replaced by cetomacrogol 1200. The average size of the microparticles is 1.5 μm, their specific weight is 0.3 g/cm³ They are taken up in 300 ml of 5% mannitol solution, which contains 0.1% cetomacrogol 1200 and 5% povidone.

Example 10

The procedure is as in Example 7, and Poloxamer 407 is replaced by 5% polysorbate 40. The average size of the microparticles is 1.0 μm, their specific weight is 0.4 g/cm³ They are taken up in 300 ml of 5% mannitol solution, which contains 1% macrogolglycerol hydroxystearate.

Example 11

The procedure is as in Example 7, and Poloxamer 407 is replaced by 5% macrogolglycerol hydroxystearate. The size of the particles is 0.9 μm and they have a specific weight of 0.3 g/cm³. They are taken up in 300 ml of 5% mannitol solution, which contains 1% macrogolglycerol hydroxystearate and 10% propylene glycol.

Example 12

The procedure is as in Example 7, and cyanoacrylic acid butyl ester is replaced by cyanoacrylic acid ethyl ester. The microparticles have an average size of 1.5 μm and a specific weight of 0.2 g/cm³. They are taken up in 300 ml of an aqueous solution of 1% Poloxamer 407 and 5% glucose.

Example 13

The procedure is as in Example 7, and cyanoacrylic acid butyl ester is replaced by cyanoacrylic acid isopropyl ester. The microparticles have an average size of 1.3 μm, and a specific weight of 0.2 g/cm³. They are taken up in 300 ml of an aqueous solution of 1% Poloxamer 407 and 5% mannitol and 10% propylene glycol.

Example 14

3 ml of cyanoacrylic acid butyl ester is dispersed in 300 ml of HCl of pH 2.0, which contains 1% Poloxamer 407, with a dissolver mixer for 120 minutes. The microparticles with an average size of 2 μm and a specific weight of 0.1 g/cm³ are separated by flotation and taken up in 5 l of a 5% mannitol solution, which contains 1% Poloxamer 407 and 10% propylene glycol.

Example 15

The procedure is as in Example 14, and Poloxamer 407 is replaced by octoxynol-9, and the pH is adjusted to 2.5. The average size of the microparticles is 0.8 μm, their specific weight is 0.15 g/cm³. They are taken up in 5 l of a 0.9% common salt solution, which contains 0.1% cetomacrogol 1200.

Example 16

The procedure is as in Example 14, and Poloxamer 407 is replaced by cetomacrogol 1200. The average size of the microparticles is 1.8 μm, their specific weight is 0.4 g/cm³. They are taken up in 5 l of a 5% glucose solution, which contains 0.2% cetomacrogol 1200.

Example 17

The procedure is as in Example 14, and Poloxamer 407 is replaced by 5% polysorbate 60. The average size of the microparticles is 1.0 μm, their specific weight is 0.4 g/cm³. They are taken up in 5 l of a 5% mannitol solution, which contains 1% Poloxamer 407 and 10% propylene glycol.

Example 8

The particles produced in Example 14, 15, 16 or 17 are taken up, instead of in solutions indicated there, in 5 l of each of a 5% mannitol solution, which contains 0.1% cetomacrogol 1200 and 5% povidone, frozen in 15 ml portions with vigorous shaking and freeze-dried. Before use, the lyophilizate is resuspended with water for injection purposes and optionally filtered.

Example 19

The particles produced in Example 14, 15, 16 or 17 are taken up, instead of in the solutions indicated there, in 5 l of a 10% lactose solution, which contains 0.1% cetomacrogol 1200, frozen in 15 ml portions with vigorous shaking and freeze-dried. Before use, the lyophilizate is resuspended with water for injection purposes and optionally filtered.

Example 20

1.0 g of hydrogenated soybean lecithin is dispersed in 200 ml of glycerol with a dissolver mixer. After 60 minutes, 2.0 g of poly-L-lactide (average molecular weight 1100), dissolved in 10 ml of boiling ethanol, is instilled in the dispersion. It is further dispersed for 60 minutes. The resulting microparticles are centrifuged at 1000 rpm, the supernatant is taken up in 50 ml of water, again centrifuged (1000 rpm), the supernatant is taken up in 5% mannitol solution. This suspension is divided into 10 ml portions and freeze-dried. Before use, the lyophilizate is resuspended with water for injection purposes.

Example 21

1.0 g of sucrose-palmitate-stearate (HLB 15) is dispersed in 200 ml of glycerol with a dissolver mixer. After 30 minutes, 1.0 g of poly-L-lactide (average molecular weight 1100), dissolved in 10 ml of boiling ethanol, is instilled in the dispersion. It is further dispersed for 60 minutes. The resulting microparticles have an average size of 2 μm. They are centrifuged at 1000 rpm for 30 minutes, the supernatant is taken up in 50 ml of water, again centrifuged (1000 rpm), the supernatant is taken up in 50 ml of a 5% mannitol solution. This suspension is divided into 10 ml portions and freeze-dried. Before use, the lyophilizate the resuspended with water for injection purposes.

Example 22

Microparticles produced according to Example 14 (250 μg/ml) in a dose of 300 μg/kg of body weight are injected in a dog (11 kg, inhalational anesthesia) perivenously at a rate of 0.1 ml/s. After 10 minutes, the liver is represented homogeneously color-coded in the color Doppler examination over a period sufficiently long for the examination.

Example 23

Example 22 is repeated with the particles produced in Examples 7-13 or 15-21. Also, in this case, the liver is homogeneously color-coded.

Example 24

Microparticles produced according to Example 8 are perivenously injected in a rabbit (3.5 kg, inhalational anesthesia) in a dose of 5 µg/kg of body weight. After 10 minutes, the liver is represented color-coded in the color Doppler examination, while tumor areas appear in the usual gray-scale values (see FIG. 1/right half of the image). For comparison, a shot in the B-mode was produced under otherwise identical conditions (see FIG. 1/left half of the image). In this shot, a uniform opacity of the liver can be seen, a differentiation of the tumor areas is no longer possible.

Example 25

4 g of terephthalic acid dichloride is dissolved in 20 ml of cyclohexane and emulsified with a propeller stirrer in 500 ml of 3% sodium carbonate solution, which contains 1% Poloxamer 407. After adding 600 mg of L-lysine, dissolved in 50 ml of 1% Poloxamer 407 solution, the capsules with an average size of 30 µm are centrifuged off, resuspended in a liquid suitable for injection, frozen and freeze-dried. After resuspension of this preparation with sterile water for injection, a suspension of gas-filled capsules of about 30 µm is present.

Example 26

6 g of human albumin is dissolved in 30 ml of distilled water and treated for 3 minutes with a rotorstator dispersing device at 20,000 rpm. With further stirring, 150 ml of a solution, containing 2% Span ® 85, of 1 part of chloroform and 4 parts of cyclohexane, is added. After 1 minute, 2 g of terephthalic acid dichloride in 20 ml of the organic solvent is added, and further stirred only with a magnetic stirrer.

After 30 minutes, the floating capsules are centrifuged off and then washed with isotonic common salt solution. A suspension of gas-filled capsules of about 30 µm is produced.

Example 27

200 ml of 5% gelatin solution of 60° C. and pH 4.5 is treated for 3 minutes with a rotor-stator dispersing device at 20,000 rpm. With constant stirring, 200 ml of a 5% gum arabic solution is added, and the batch is cooled to 5° C. After 2 hours, 50 ml of a 3% glutaraldehyde solution is added, and the pH is adjusted to 8.5. The floating capsules with a size of 20–50 µm are centrifuged off and washed several times with isotonic common salt solution, which contains 0.1% Poloxamer 188.

Example 28

A solution of 99.5 g of water and 0.5 g of Poloxamer 407 is adjusted with 1N hydrochloric acid to pH 2.4. 1.0 g of cyanoacrylic acid butyl ester is added to this solution with stirring (4000 rpm) and further stirred for 60 minutes. The obtained suspension is neutralized, the gas-filled capsules with a size of about 30–100 µm are separated by centrifugation and resuspended in a liquid suitable for administration.

Example 29

Figure 3:
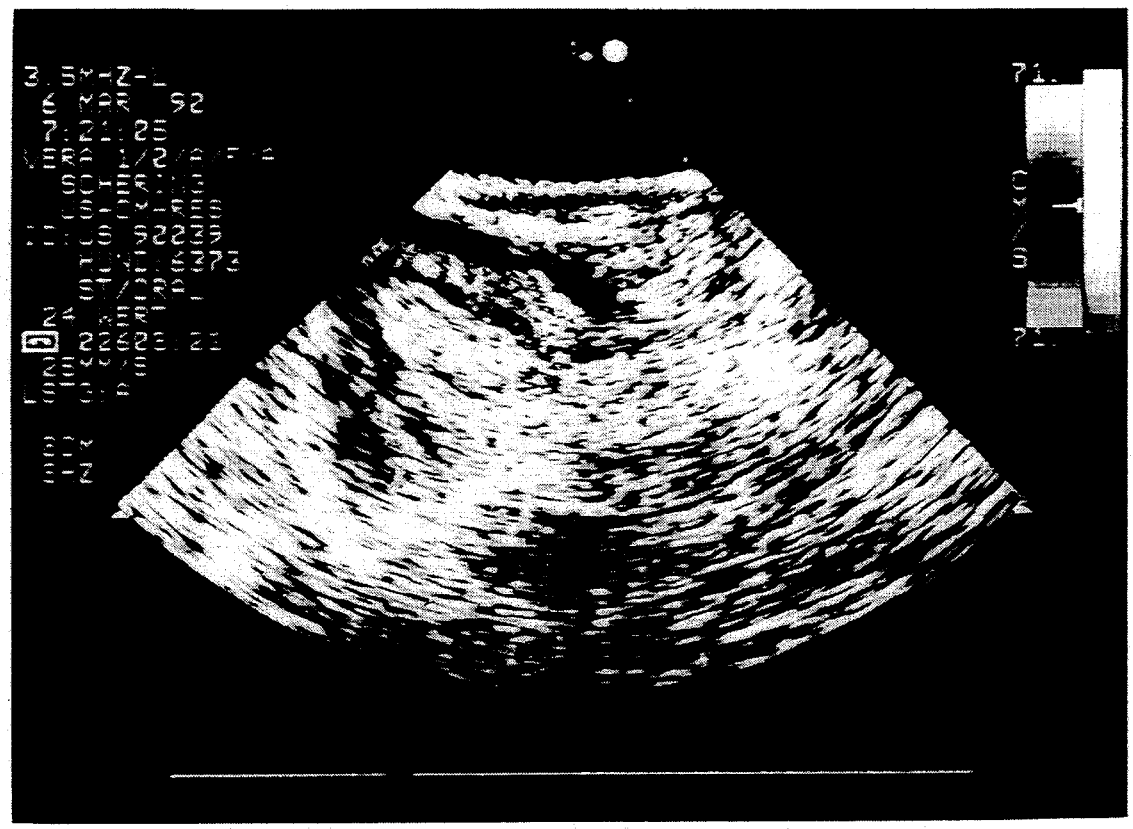

30 ml of a suspension of gas-filled microparticles, which were produced according to Example 27, is administered to a 10 kg anesthetized beagle dog by a stomach tube. The concentration is 1 mg/ml of suspension. Directly after administration, the stomach is examined with a color Doppler ultrasonic device. The lumen is represented colored (FIG. 2). 30 minutes later, the small intestine is also labeled (FIG. 3).

Example 30

3 ml of microcapsules, produced according to Example 26, of conc. $10^9$ particles/ml is administered to an anesthetized beagle dog by a bladder catheter in the liquid-filled bladder. In FIG. 4, the effect before and after the administration of contrast media is represented in the color Doppler mode.

Example 31

100 ml of 0.01N HCl, which contains 1% of polyoxyethylene polyoxypropylene polymer having a molecular weight of 12,000 (Pluronic ® F 127), is mixed for 1 minute with a high-speed rotor-stator mixer. 800 mg of cyanoacrylic acid butyl ester is added to the resulting gas bubble suspension and stirred for 5 minutes more. After completion of the polymerization, the suspension is neutralized with 0.1N NaOH and isotonized with sodium chloride. The suspension contains about $3 \times 10^9$ gas-containing microparticles per ml. Images obtained with the resultant particles are especially good.

Example 32

Figure 5:
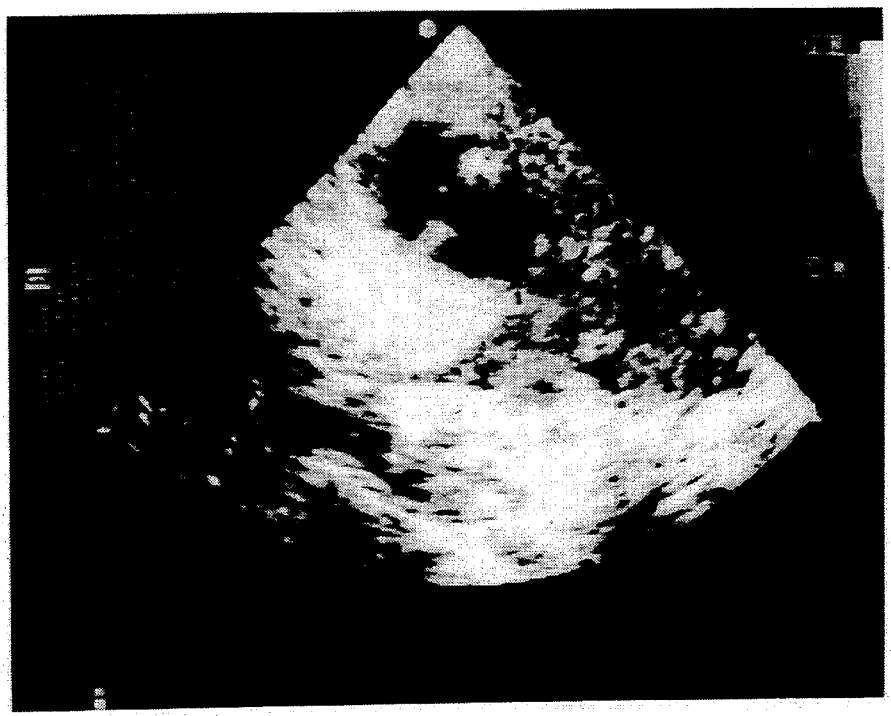
FIG. 5 is a color Doppler image of a hare's liver (Example 32)

Microcapsules, produced according to example 4 (400 mg α-cyano acrylic acid butyl ester dissolved in 0.4 ml methylene chloride and emulsified in 60 ml 0.01N HCl which contained Pluronic ® F 127) were administered to hare rabbits (3.5 kg, inhalation anesthesia) in a concentration of 500 micrograms/ml in a dose of 2 mg/kg body weight by the marginal vein of the ear at a rate of 2 ml/min. After 60 min. the liver was examined with color Doppler. The results are shown in the image identified as FIG. 5.

Example 33

Figure 6:
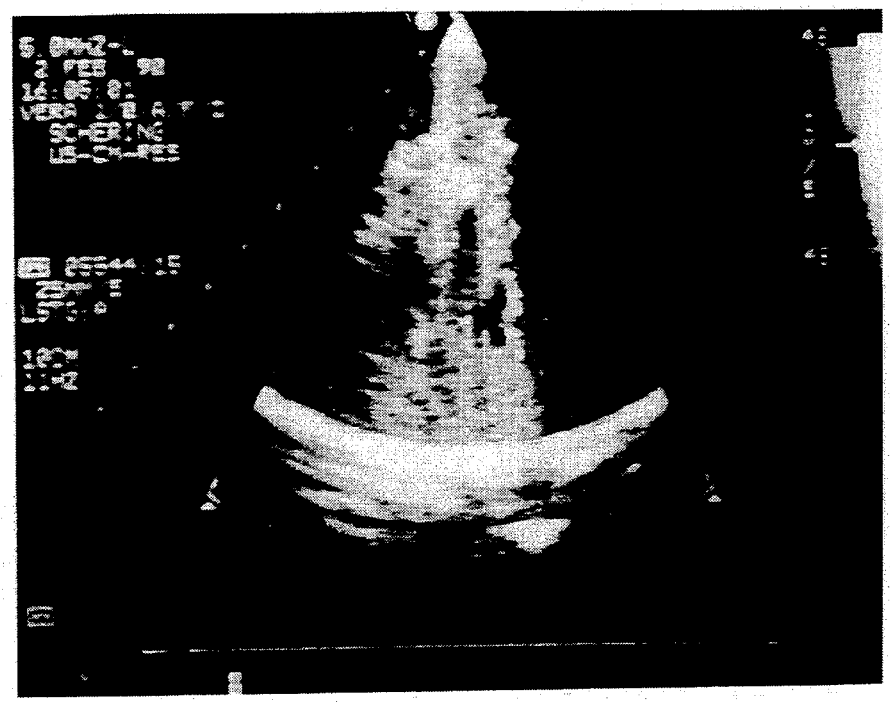
FIG. 6 is a color Doppler image of a gelatin block (Example 33)

To a 200 ml 3% gelatin solution are mixed 500 micrograms of microcapsules produced according to example 2 above, which were previously taken up in 1 ml of isotonic common salt solution, at 45° C. After cooling and setting of the gelatin, strong color signals are produced in the examination of the gelatin block with color Doppler, as represented by the image identified as FIG. 6.

Example 34

Figure 7:
FIG. 7 is a color Doppler image of a dog's liver (Example 34)

Microcapsules, produced according to example 3 above (200 mg cyanoacrylic acid butyl ester) are injected in a dog (12.5 kg, inhalation anesthesia) in a dose of 1 mg/kg body weight, in a peripheral vein, at a rate of 2 ml/min. After 30 min. the liver is examined with the color Doppler and an image obtained. (See FIG. 7.)

Example 35

Figure 8:
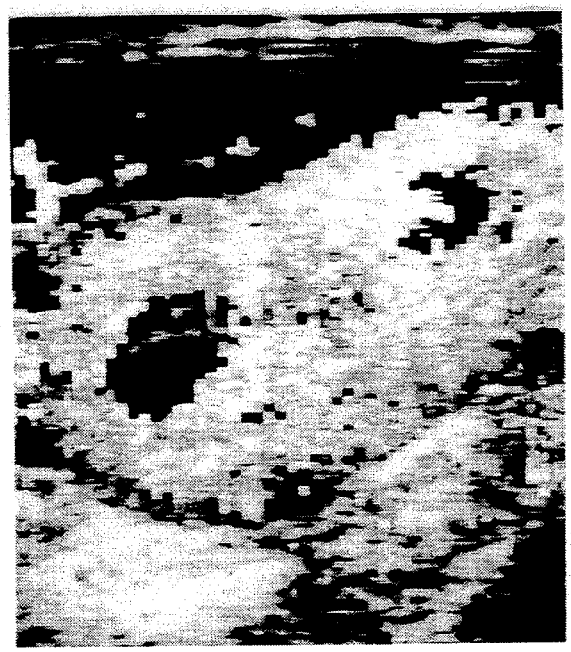
FIG. 8 is a color Doppler image of a dog's kidney (Example 35).

Microcapsules, produced according to example 4 above (400 mg α-cyanoacrylic acid butyl ester dissolved in 0.4 ml of methylene chloride) are injected in a dog (10.8 kg, inhalation anesthesia) in a dose of 0.3 mg/kg body weight, in a peripheral vein, at a rate of 2 ml/min. After 1 min. the kidney is examined with an angiodynamograph. The results are shown in the image identified as FIG. 8.

Example 36

3 nl of cyanacrylic acid butyl ester is dispersed in 300 ml of HCl of pH 2.5, which contains 1% nonoxynol, with a dissolver-mixer for 90 minutes. The microparticles with an average size of 1.4 m are separated by flotation, taken up in 100 ml of water and then mixed with 5% albumin. Then, it is frozen in 5 ml portions under light agitation and freeze-dried.

Example 37

3 nl of cyanacrylic acid butyl ester is dispersed in 300 ml of HCl of pH 2.5, which contains 1% octoxynol, with a dissolver-mixer for 90 minutes. The microparticles with an average size of 1.4 $\mu$m are separated by flotation, taken up in 100 ml of 5% autoclaved gelatin solution adjusted with HCl/NaOH to pH 5.0 and then frozen in 5 ml portions under light agitation as well as freeze-dried.

Example 38

3 nl of cyanacrylic acid butyl ester is dispersed in 300 ml of HCl of pH 2.5, which contains 1% octoxynol and 5% povidone, with a dissolver-mixer for 90 minutes. The microparticles with an average size of 1.4 $\mu$m are separated by flotation, taken up in 5% povidone solution and bottled in 5 ml portions. Then, the bottled suspension is thermostated for one hour to 0° C. and frozen as well as freeze-dried.

Example 39

3 nl of cyanacrylic acid butyl ester is dispersed in 300 ml of HCl of pH 2.5, which contains 1% octoxynol, with a dissolver-mixer for 90 minutes. The microparticles with an average size of 1.4 $\mu$m are separated by flotation, taken up in 300 ml of water, mixed with 0.1% glycerol and 10% lactose and, after freezing, freeze-dried.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of obtaining an ultrasonic image of a patient comprising administering to the patient microparticles comprising a cavity containing a gas or a volatile fluid, which particles upon exposure to an effective color Doppler sonography modality produce a Doppler signal when the particles are essentially motionless in the patient, and imaging said patient with an effective ultrasonic color Doppler modality in a region where said microparticles are essentially motionless.

2. A method of claim 1, comprising administering microparticles which comprise a polymeric material having entrapped therein gases and/or fluids having a boiling point below 60° C. in free or bonded form and-/or microbubbles comprising a gelatin or albumin microcapsule having a gas or volatile fluid entrapped therein.

3. A method of claim 2, comprising administering microparticles which are gas-filled gelatin microcapsules.

4. A method of claim 2, comprising administering microparticles which are gas-filled microcapsules having walls comprising denatured protein.

5. A method of claim 4, wherein the denatured protein is denatured albumin or human serum albumin.

6. A method of claim 1, comprising administering microparticles which are gas- or liquid-filled microcapsules having walls of a biodegradable polyester of a gas- or liquid-filled polycyanoacrylate or a biodegradable polyester of an $\alpha$-, $\beta$- or $\gamma$-hydroxycarboxylic acid.

7. A method of claim 1, comprising administering microparticles which are gas- or liquid-filled microcapsules having walls of a biodegradable polyaldehyde which optionally contains additives and/or crosslinks capable of copolymerization, surfactants or surfactant mixtures, coupling agents or biomolecules or macromolecules optionally bound by these coupling agents.

8. A method of claim 1, wherein the region where said microparticles are essentially motionless is in the reticuloendothelial system.

9. A method as in claim 1, wherein the region where said microparticles are essentially motionless is in the myocardium.

10. A method as in claim 1, wherein the region where said microparticles are essentially motionless is in the GI tract.

11. A method as in claim 1, wherein the region where said microparticles are essentially motionless is in the lymphatic system, liver or spleen.

12. A method as in claim 1, comprising administering microparticles which are administered in an amount which provides $10^5$-$10^7$ microparticles per cm$^3$ of the tissue to be imaged.

13. A method as in claim 1, comprising administering microparticles by peroral, intraarticular, intravesical, transvaginal, intraperitoneal or intravenous administration.

14. A method according to claim 1, comprising administering microparticles which contain a gas which is air, nitrogen, oxygen, carbon dioxide, hydrogen, ammonia, ethylene, methane, ethane, propane, butane or a mixture thereof.

15. A method according to claim 1, wherein the patient is imaged with effective ultrasonic radiation and the Doppler effects are photographically recorded as a change in color.

16. A method of obtaining an ultrasonic image of a patient comprising administering to the patient, microparticles comprising a cavity containing a volatile fluid which particles become sited in tissue or a body cavity of said patient and become essentially motionless therein, irradiating such tissue or cavity with an ultrasound frequency of a strength effective to burst said particles and imaging said patient by recording the ultrasound frequencies scattered as a result of said bursting.

17. A method of claim 16, comprising administering microparticles which are gas- or liquid-filled microcapsules having walls of a biodegradable polyester of a gas- or liquid-filled polycyanoacrylate or a biodegradable polyester of an $\alpha$-, $\beta$- or $\gamma$-hydroxycarboxylic acid.

18. A method of claim 16, comprising administering microparticles which are gas- or liquid-filled microcapsules having walls of a biodegradable polyaldehyde, which optionally contains additives and/or crosslinks capable of copolymerization, surfactants or surfactant mixtures, coupling agents or biomolecules or macromolecules optionally bound by these coupling agents.

19. A method of claim 16, wherein the region where said microparticles are essentially motionless is in the reticuloendothelial system, the myocardium or the GI tract.

* * * * *